United States Patent [19]

Anthony

[11] 4,402,904

[45] Sep. 6, 1983

[54] METHOD FOR DETERMINING CLAD INTEGRITY OF A NUCLEAR FUEL ROD

[75] Inventor: Andrew J. Anthony, Tariffville, Conn.

[73] Assignee: Combustion Engineering, Inc., Windsor, Conn.

[21] Appl. No.: 217,713

[22] Filed: Dec. 18, 1980

[51] Int. Cl.³ .............................................. G21C 17/06
[52] U.S. Cl. ..................................... 376/251; 376/450; 73/336.5; 436/149
[58] Field of Search .................... 376/450, 251, 252; 73/336, 336.5, 52, 779; 23/230 L, 232 E; 338/34; 436/149

[56] References Cited

U.S. PATENT DOCUMENTS

| | | | |
|---|---|---|---|
| 3,037,924 | 6/1962 | Creutz | 376/450 |
| 3,141,830 | 7/1964 | Klepfer . | |
| 3,625,823 | 12/1971 | Kerr et al. . | |
| 3,666,625 | 5/1972 | Nybo | 376/450 |
| 3,813,286 | 5/1974 | Goldman et al. | 376/251 |
| 3,823,068 | 7/1974 | Worlton et al. | 376/450 |
| 3,846,235 | 11/1974 | Jones et al. | 376/450 |
| 3,899,392 | 8/1981 | Grossman et al. . | |
| 3,940,313 | 2/1976 | Steven | 376/450 |

FOREIGN PATENT DOCUMENTS

| | | | |
|---|---|---|---|
| 50-23758 | 9/1975 | Japan | 338/34 |
| 54-148596 | 11/1979 | Japan | 338/34 |
| 55-1530 | 1/1980 | Japan | 338/34 |

Primary Examiner—Harvey E. Behrend
Attorney, Agent, or Firm—L. James Ristas

[57] ABSTRACT

A method for testing the clad integrity of a nuclear fuel rod, comprising the first step of fabricating a sealed fuel rod with a wad of electrically conducting material mounted therein. The material is of a type that undergoes a permanent change in electrical conductivity when exposed to water. The next step is to establish an eddy current signal characteristic of the moisture-free rod. The rod is then loaded into the core as part of a fuel assembly. After the producing power, the assembly is removed for inspection, and an eddy current signal is again obtained from the rod. The eddy current signals are compared to determine whether inleakage of moisture has oxidized or otherwise altered the conductivity of the wad enough to significantly change the characteristic signal.

2 Claims, 2 Drawing Figures

METHOD FOR DETERMINING CLAD INTEGRITY OF A NUCLEAR FUEL ROD

BACKGROUND OF THE INVENTION

This invention relates to nuclear reactor fuel, and more particularly to the inspection for failure of cladded nuclear fuel rods.

In modern light-water nuclear power reactors, the reactor core typically consists of over one hundred closely spaced fuel assemblies, each assembly containing an array of over one hundred individual fuel rods. The fuel rods are typically elongated, sealed tubes of Zircaloy containing a column of uranium dioxide pellets. Safe operation of the reactor requires that the integrity of the Zircaloy clad be maintained throughout the burnup history of each fuel rod. Occasionally, however, the clad is perforated during operation. Although each fuel assembly typically burns for a total of about three cycles, or about three years, the assemblies in the reactor core are usually rearranged annually during the refueling process. During refueling, the assemblies may be removed from the core and inspected for failed fuel. This inspection is typically very complicated and time consuming because the inspection must be performed remotely under water and because most of the rods in the assembly are not on the assembly periphery and thus not readily accessible. It would be far too costly to disassemble, inspect, and reconstitute every assembly suspected of containing one or more leaking fuel rods. What is needed is a method for quickly inspecting all fuel rods in an assembly to identify those in which cladding has been breached, permitting coolant water to enter the rod.

SUMMARY OF THE INVENTION

It is thus an object of the present invention to provide a method for quickly and simply identifying failed fuel rods during routine refueling operations.

It is a further object that the method be compatible with existing fuel and fuel assembly designs, and not require significant materials or fabrication cost increases to existing fuel designs.

According to the invention, a method for testing the clad integrity of a nuclear fuel rod is provided, comprising the first step of fabricating a sealed fuel rod with a wad of electrically conducting material mounted therein. The material is of a type that undergoes a permanent change in electrical conductivity when exposed to water. The next step is to establish an eddy current signal characteristic of the moisture-free rod. The rod is then loaded into the core as part of a fuel assembly. After producing power, the assembly is removed for inspection, and an eddy current signal is again obtained from the rod. The eddy current signals are compared to determine whether inleakage of moisture has oxidized or otherwise altered the conductivity of the wad enough to significantly change the characteristic signal.

In the preferred embodiment a zirconium wool similar to that found in conventional photographic flash bulbs is secured to the upper end caps of each nuclear fuel rod and is exposed to the plenum region above the fuel pellets. Any inleakage of water oxidizes the wool and transforms it into a powder that in effect vanishes from the cap and plenum. The eddy current signal corresponding to this oxidized condition is dramatically different from the characteristic signal for a moisture-free rod containing the zirconium wool.

Since the upper ends of the fuel rods in an assembly are typically accessible during refueling, and since the probe signal corresponding to a failed rod is readily identifiable to the probe operator, the inspection of each assembly can be simply and conveniently completed within a short time. It is not necessary to remove or left any rods and they can be inspected simultaneously in large quantity.

BRIEF DESCRIPTION OF THE DRAWINGS

The invention may be more fully understood in the context of the best mode for carrying it out as described hereinbelow in conjunction with the accompanying drawings in which.

DESCRIPTION OF THE PREFERRED EMBODIMENT

Figure 1:
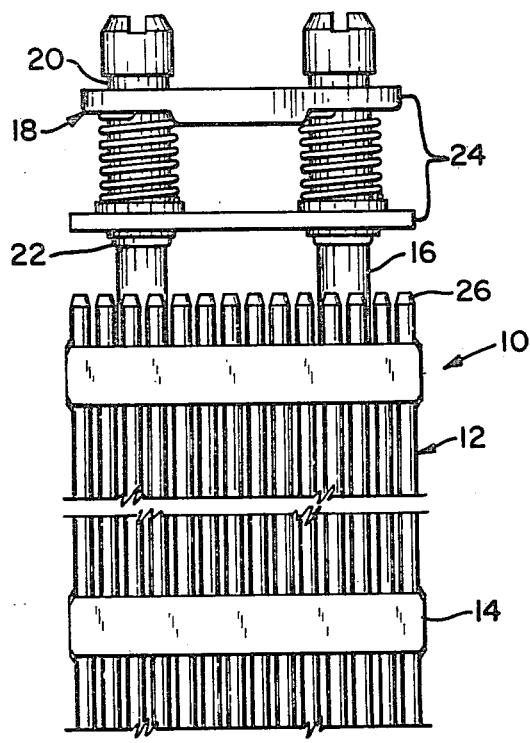
FIG. 1 is an elevation view of a portion of a typical nuclear fuel assembly.

FIG. 1 illustrates the upper portion of a nuclear fuel assembly 10 including a square array of Zircaloy clad fuel rods 12 carried and supported by a series of axially spaced, square grids 14 which are fixedly connected to a plurality of guide tubes 16. The upper end fitting 18 includes a locking post 20 which is screwed into a boss 22 on the guide tube 16, and a coil spring system 24 for holding the assembly in place during reactor operation.

During a typical reactor refueling, each assembly is at some point removed from the core and supported under water where inspection of the fuel rods can be made. It should be appreciated that the fuel rods 12 located deep within the 14×14 array cannot be easily inspected. If, for example, it is suspected that at least one rod 12 within the array is leaking, it may be necessary to disassemble the assembly to isolate and verify the failed rod. In the illustrated assembly 10, the posts 20 may be unscrewed and, together with the spring system 24, lifted off the assembly to expose the end caps 26 of the fuel rods. The suspect rods may then be lifted out of the assembly and inspected for failure.

Figure 2:
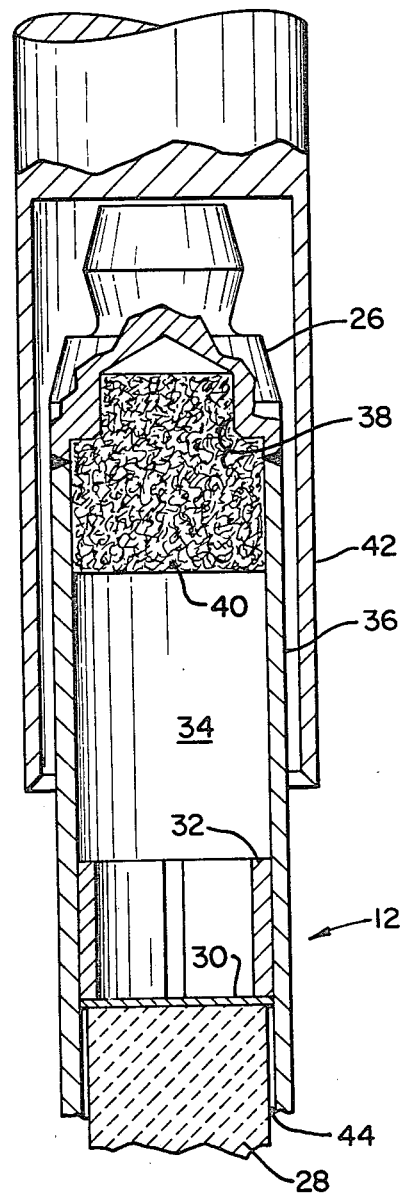
FIG. 2 is a partially sectioned view of a nuclear fuel rod with a schematic representation of the associated eddy current probe, according to the invention.

According to the present invention as shown in FIG. 2, a simpler method of quickly and easily identifying failed fuel rods avoids the inconveniences and delays associated with conventional fuel inspection techniques. A single fuel rod 12 is shown in partial section to reveal a fuel pellet 28, a disc 30, and a "C" type resilient member 32 for maintaining a downward bias on the pellet column. A plenum region 34 is provided within the upper end of the Zircaloy tube or clad 36, which is sealed with a welded Zircaloy end cap 26. Connected to a cavity 38 within the end cap 26 and extending into the plenum 34 is a wad or compact 40 of the zirconium wool. The change in the electrical conductivity of the wad 40 resulting from excessive moisture due to fuel rod failure, forms the basis of the present invention. The change in conductivity can be readily determined by conventional eddy current equipment as represented by the probe 42.

Referring also to FIG. 1, in the preferred mode for carrying out the invention, each new fuel rod 12 fabricated for inclusion in a fresh assembly 10 is sealed with an end cap 26 which has mounted therein a wad or compact 40 of a porous or fibrous, electrically conducting metallic material of a type that undergoes a permanent change in electrical conductivity when exposed to water. Since fuel failure would generally occur, if at all, while the fuel rod 12 is generating power in a nuclear reactor core, the wad transformation mechanism begins with coolant water or water vapor entering the rod 12 somewhere along its active length and immediately being superheated in the gap 44 by contact with the fuel pellet surface 28, which is typically at about 1500° F. (816° C.). The water vapor rises through the gap 44, which is typically at least 1000° F. (538° C.), to the plenum region 34 where it contacts and oxidizes the wad 40, which is typically at a temperature of at least 750° F. (399° C.). Thus, the conductivity of the wad 40 should be permanently altered at these conditions, even if no significant transformation would occur at ambient conditions. Zirconium, zirconium ferrite, and other zirconium based materials are suitable, and other metals may be suitable to varying degrees.

After the requisite number of fuel rods 12 have been fabricated, they are bound together to form a fresh fuel assembly 10. Either before or after the fuel rods are bound into an assembly, but before the assembly is loaded into the reactor core, an eddy current probe 42 is placed around the end cap 26 of at least one of the fuel rods and an external scan is made. The output signal characteristic of a dry (less than about 10 ppm $H_2O$), newly fabricated fuel rod is thus established. With a zirconium wool compact 40, the difference in probe signals between a dry rod and a failed rod is so dramatic that only one base reading for a dry rod need be made. The probe output signals for all other dry rods will be quite similar.

The assembly 10 is then placed in a nuclear reactor core where it will generate fission power through at least one burnup cycle. Between cycles the core is refueled and the assemblies may be inspected. Usually, the assemblies are individually inspected in a pool outside the reactor vessel. With the present invention, the eddy current probe 42 is placed over every end cap 26 of the assembly to determine whether any rod has failed. Rod failure is evidenced by the significantly different probe output signals obtained when the zirconium wool has become electrically nonconducting zirconium oxide. The wad may even become powdery and disappear from the plenum as it falls down along the pellet column.

In FIG. 1 it may be seen that with the typical fuel assembly illustrated, a space is provided between the end caps 26 and the parts of the upper end fitting 24 that obstruct direct access to the end caps from above the assembly. In this assembly all fuel rods 12 in the square array may be inspected by a suitably angled probe 42. Preferably, many rods 12 are inspected simultaneously using a plurality of probes 42. If some rods 12 are not accessible, the upper end fitting 18 may be removed to expose the end caps 26, by unscrewing the locking post 20 and lifting the spring system 24. Despite this inconvenience, however, the present permits inspection of all fuel rods 12 in the array without the need to pull any rods out of the assemblies 10. With conventional techniques which rely on inspection of the entire rod surface, even the removal of the spring system 24 would not expose the interior rods for inspection along their entire lengths.

When, as in the preferred embodiment, a single dry rod inspection is relied upon to establish a characteristic signal for a multiplicity of rods in many assemblies 10, all rods 12 should, of course, contain wads 40 that have approximately the same general shape and mass.

It should be appreciated that the invention is not limited to the foregoing embodiment. For example, the wad 40 may be located elsewhere in the rod 12, such as the bottom, if this location is more acessible for post-irradiation inspection. The tube could be made of stainless steel or other conducting metal. Also, the invention can be adapted for inspecting fuel rods or other sealed tubes during manufacturing to determine whether the rods have unacceptably high water or water vapor content. The choice of wad material and surface-to-volume ratio for the wad should depend on the conditions under which water at a relatively higher pressure would leak into a defective rod.

I claim:

1. A method for testing the clad integrity of a nuclear fuel rod comprising the steps of:
    (a) fabricating a sealed nuclear fuel rod with a cap seal at one end, the cap having a cavity therein, said cavity having connected therewithin a wad of fibrous zirconium or zirconium ferrite;
    (b) externally scanning the rod with an eddy current probe at the location of the wad to establish a probe output signal characteristic of the moisture-free rod;
    (c) placing the rod in a water environment in which the external water pressure is greater than the internal pressure of the rod;
    (d) externally scanning the rod with an eddy current probe at the location of the wad;
    (e) comparing the probe output signals of steps (b) and (d) to determine whether the conductivity of the wad has changed, indicating the ingress of water through the clad.

2. A method for identifying perforated nuclear fuel rods in a nuclear fuel assembly comprising the steps of:
    (a) fabricating a plurality of sealed nuclear fuel rods, each having a cap seal at one end, the cap having a cavity therein, said cavity having connected therewithin a wad of fibrous zirconium or zirconium ferrite;
    (b) fabricating a fuel assembly by securing together said plurality of fuel rods in spaced parallel relationship;
    (c) externally scanning said one end of at least one fuel rod with an eddy current probe to establish a probe output signal characteristic of a moisture-free fuel rod;
    (d) irradiating the fuel assembly in a water cooled nuclear power reactor;
    (e) externally scanning said one end of each of the fuel rods in the assembly with an eddy current probe;
    (f) comparing the probe output signals from step (e) with the characteristic signal for a moisture free rod as established in step (c);
    (g) identifying any leaking fuel rods in the fuel assembly by the affect on the probe signal due to the permanent change in wad conductivity resulting from the oxidation of said wad material.

* * * * *